(12) United States Patent
Halderman et al.

(10) Patent No.: US 12,313,959 B2
(45) Date of Patent: May 27, 2025

(54) IMAGE CAPTURE DEVICE WITH REDUCED FOGGING

(71) Applicant: INTUITIVE SURGICAL OPERATIONS, INC., Sunnyvale, CA (US)

(72) Inventors: Jonathan Halderman, Sunnyvale, CA (US); John A Barton, San Jose, CA (US); Mathew Clopp, Santa Clara, CA (US); Rumen Deyanov, Fremont, CA (US); Anqi Fan, Sunnyvale, CA (US); Yves Lacroix, San Jose, CA (US); Derek C. Liou, Cupertino, CA (US); Theodore W. Rogers, Alameda, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/316,958

(22) Filed: May 12, 2023

(65) Prior Publication Data

US 2024/0004273 A1    Jan. 4, 2024

Related U.S. Application Data

(63) Continuation of application No. 16/336,741, filed as application No. PCT/US2017/056595 on Oct. 13, 2017, now Pat. No. 11,686,995.

(Continued)

(51) Int. Cl.
*A61B 1/00* (2006.01)
*A61B 1/05* (2006.01)
(Continued)

(52) U.S. Cl.
CPC ............ *G03B 17/55* (2013.01); *A61B 1/0008* (2013.01); *A61B 1/00163* (2013.01); *A61B 1/05* (2013.01);
(Continued)

(58) Field of Classification Search
CPC .......... A61B 1/127; A61B 1/126; A61B 1/253; A61B 1/00163; A61B 1/07; A61B 1/128;
(Continued)

(56) References Cited

U.S. PATENT DOCUMENTS 4,279,246 A    7/1981   Chikama
4,918,521 A *  4/1990   Yabe ..................... H04N 23/54
                                                600/109

(Continued)

FOREIGN PATENT DOCUMENTS

CN        102307511 A       1/2012
CN        203468568 U       3/2014
(Continued)

OTHER PUBLICATIONS

Extended European Search Report for Application No. EP17861130.7, mailed on Apr. 28, 2020, 7 pages.
(Continued)

*Primary Examiner* — Aaron B Fairchild
(74) *Attorney, Agent, or Firm* — Haynes & Boone, LLP.

(57) ABSTRACT

An image capturing device comprises a first elongated body portion formed of a first material and a second elongated body portion coupled to a proximal end of the first body portion. The second body portion is formed of a second material having a greater heat conductivity than the first material. The device further comprises an imaging window coupled to a distal end of the first body portion, a first housing within the first body portion, an image sensor mounted to the first housing, and an image processor mounted to the first housing and coupled to receive electrical signals from the image sensor. The device further comprises a second housing within the first body portion. The second housing is coupled to the first housing and to the window such that heat generated by the image sensor and image (Continued)

processor is transmitted through the second housing to the window.

16 Claims, 11 Drawing Sheets

Related U.S. Application Data

(60) Provisional application No. 62/408,332, filed on Oct. 14, 2016.

(51) Int. Cl.
| | |
|---|---|
| *A61B 1/07* | (2006.01) |
| *A61B 1/12* | (2006.01) |
| *A61B 34/00* | (2016.01) |
| *A61B 34/35* | (2016.01) |
| *A61B 90/00* | (2016.01) |
| *G02B 23/24* | (2006.01) |
| *G03B 15/14* | (2021.01) |
| *G03B 17/55* | (2021.01) |

(52) U.S. Cl.
CPC ............... *A61B 1/07* (2013.01); *A61B 1/127* (2013.01); *A61B 1/128* (2013.01); *A61B 34/35* (2016.02); *A61B 34/74* (2016.02); *A61B 90/361* (2016.02); *G02B 23/2423* (2013.01); *G03B 15/14* (2013.01); *A61B 2034/742* (2016.02)

(58) Field of Classification Search
CPC ....... A61B 34/35; A61B 34/74; A61B 90/361; A61B 2034/742; A61B 34/30; A61B 34/37; A61B 1/015; A61B 1/0008; A61B 1/05; A61B 1/051; A61B 1/12; A61B 1/18; G02B 23/2423; G03B 15/14; G03B 17/55
USPC ......................................................... 600/169
See application file for complete search history.

(56) References Cited

U.S. PATENT DOCUMENTS

| | | | |
|---|---|---|---|
| 5,746,737 A | 5/1998 | Saadat | |
| 6,493,608 B1 | 12/2002 | Niemeyer | |
| 6,671,581 B2 | 12/2003 | Niemeyer et al. | |
| 6,817,974 B2 | 11/2004 | Cooper et al. | |
| 2002/0128535 A1* | 9/2002 | Kikuchi | A61B 1/051 |
| | | | 600/101 |
| 2002/0135694 A1 | 9/2002 | Williams | |
| 2005/0245789 A1* | 11/2005 | Smith | A61B 1/0016 |
| | | | 137/560 |
| 2006/0173243 A1* | 8/2006 | Watanabe | A61B 1/04 |
| | | | 600/141 |
| 2008/0228035 A1 | 9/2008 | Hagihara et al. | |
| 2008/0300457 A1* | 12/2008 | Hosaka | A61B 1/00096 |
| | | | 600/110 |
| 2009/0264701 A1 | 10/2009 | Ito | |
| 2010/0168520 A1 | 7/2010 | Poll et al. | |
| 2010/0198009 A1 | 8/2010 | Farr et al. | |
| 2010/0292538 A1* | 11/2010 | Hirata | A61B 1/00071 |
| | | | 600/129 |
| 2014/0200406 A1 | 7/2014 | Bennett et al. | |
| 2014/0221743 A1 | 8/2014 | Sugiyama et al. | |
| 2014/0276577 A1 | 9/2014 | Thralls | |
| 2015/0105791 A1 | 4/2015 | Truckai | |
| 2015/0238072 A1 | 8/2015 | Makmel | |
| 2016/0081541 A1* | 3/2016 | Yasue | G02B 23/2476 |
| | | | 600/169 |
| 2017/0258309 A1 | 9/2017 | Deyanov | |
| 2020/0077878 A1 | 3/2020 | Halderman et al. | |

FOREIGN PATENT DOCUMENTS

| | | |
|---|---|---|
| CN | 103874450 A | 6/2014 |
| CN | 204468021 U | 7/2015 |
| CN | 204906513 U | 12/2015 |
| CN | 205386130 U | 7/2016 |
| WO | WO-9731293 A1 | 8/1997 |

OTHER PUBLICATIONS

International Preliminary Report on Patentability and Written Opinion for Application No. PCT/US2017/056595, mailed on Apr. 25, 2019, 11 pages.
International Search Report and Written Opinion for Application No. PCT/US2017/056595, mailed on Jan. 15, 2018, 15 pages.
Vertut, J, and Coiffet. P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP24176838.1, mailed on Oct. 22, 2024, 07 pages.

* cited by examiner

IMAGE CAPTURE DEVICE WITH REDUCED FOGGING

RELATED APPLICATIONS

This patent application is the continuation of U.S. patent application Ser. No. 16/336,741, filed, Mar. 26, 2019, which is the U.S. national phase of International Application No. PCT/US2017/056595, filed Oct. 13, 2017, which designated the U.S. and claims priority to and the benefit of the filing date of U.S. Provisional Patent Application 62/408,332, entitled "IMAGE CAPTURE DEVICE WITH REDUCED FOGGING," filed Oct. 14, 2016, all of which are incorporated by reference herein in their entirety.

TECHNICAL FIELD

The present disclosure is directed to image capturing devices for conducting an image-guided procedure and more particularly to a systems and methods for maintaining visibility while the image capture device is inserted within a patient.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery. During the performance of a medical procedure, it is useful to view two or three dimensional live images of the surgical site captured by an image capturing device positioned within the patient anatomy. Often the imaging window of the device becomes fogged due to the environmental conditions within the patient anatomy. Image capturing devices are needed that reduce condensation on the window to allow for recording of a clear image.

SUMMARY

The embodiments of the invention are best summarized by the claims that follow the description.

In some examples, an image capturing device comprises an elongated body, an imaging window coupled to a distal end of the elongated body, and a heat source within the elongated body. The heat source is configured to apply heat to the imaging window to remove condensation from or prevent condensation from forming on the imaging window.

In some examples, an image capturing device comprises an elongated body, an imaging window coupled to a distal end of the elongated body, and an ultrasonic transducer within the elongated body. The ultrasonic transducer is configured to apply ultrasonic energy to the imaging window.

In some examples, an image capturing device comprises a first elongated body portion formed of a first material and a second elongated body portion coupled to a proximal end of the first elongated body portion. The second elongated body portion is formed of a second material. The second material has a greater heat conductivity than the first material. The image capturing device also comprises an imaging window coupled to a distal end of the first elongated body portion The image capturing device also comprises a first housing within the first elongated body portion with an image sensor mounted to the first housing. The image capturing device also comprises an image processor mounted to the first housing and coupled to receive electrical signals from the image sensor. The image capturing device also comprises a second housing within the first elongated body portion. The second housing is coupled to the first housing and to the window such that heat generated by the image sensor and image processor is transmitted through the second housing to the imaging window.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

Figure 1:
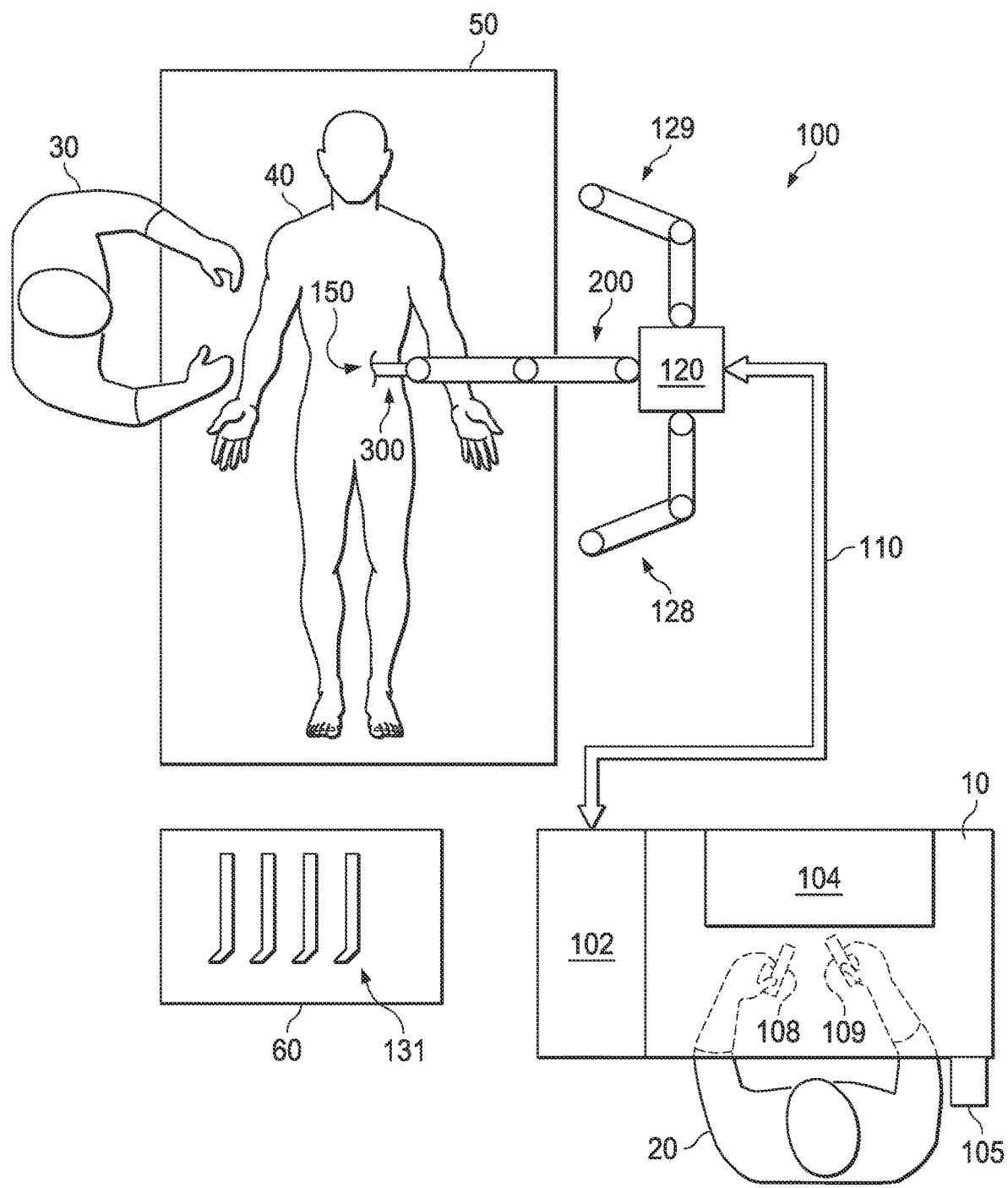
FIG. 1 is a simplified diagram of an operating room employing a medical teleoperational system with a bundled unit of medical devices according to some embodiments.

FIG. 1 illustrates, as an example, a top view of an operating room in which a medical teleoperational system 100 is being utilized by a Surgeon 20 for performing a medical procedure on a Patient 40 who is lying down on an operating table 50. One or more Assistants 30 may be positioned near the Patient 40 to assist in the procedure while the Surgeon 20 performs the procedure teleoperatively by manipulating control devices 108, 109 on a surgeon console 10.

A medical teleoperational system 100 is equipped with teleoperational arm assemblies 128, 129, 200 which are mounted on a patient side cart 120. In the present example, a bundled unit 300 of medical devices is inserted through a single entry port 150 into the Patient 40. Although the entry port 150 is a minimally invasive incision in the present example, in the performance of other medical procedures, it may instead be a natural body orifice. The bundled unit 300 is held and manipulated by the teleoperational arm assembly. Only the teleoperational arm assembly 200 is used in the present example. Teleoperational arm assemblies 128, 129 are swung out of the way during the performance of the present medical procedure, because they are not being used.

The console 10 includes a monitor 104 for displaying an image (e.g., a 2-D or 3-D image) of a surgical site to the Surgeon 20, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the console 10 or positioned next or near to it, or it may comprise a number of processing or controller components that are distributed in a distributed processing fashion throughout the system 100.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
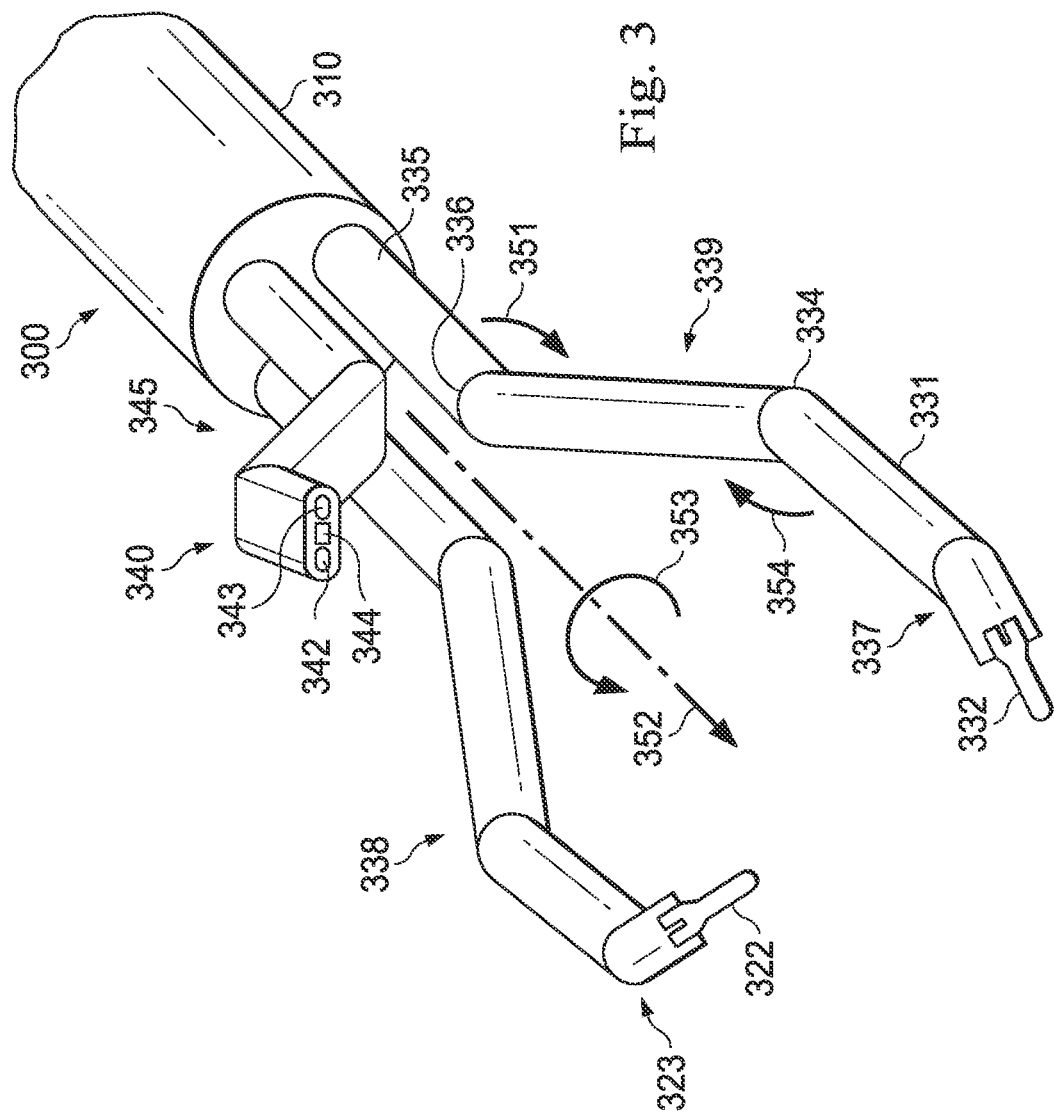
FIG. 3 is a simplified diagram of a distal end of a bundled unit of medical devices according to some embodiments.

As shown in FIG. 3, the bundled unit 300 may include two surgical instruments or tools 338, 339 and an image capturing device 340. Each of the surgical tools 338, 339 is associated with one of the control devices 108, 109. The Surgeon performs a medical procedure by manipulating the control devices 108, 109 so that the processor 102 causes corresponding movement of their respectively associated surgical tools 338, 339, while the Surgeon views the surgical site in 3-D on the console monitor 104 as it is captured by the image capturing device 140.

Control devices 108, 109 may be provided with at least the same degrees of freedom as their associated tools 338, 339 to provide the Surgeon with telepresence, or the perception that the control devices 108, 109 are integral with the tools 338, 339 so that the Surgeon has a strong sense of directly controlling the tools 338, 339.

The monitor 104 may be positioned near the Surgeon's hands so that it will display a projected image that is oriented so that the Surgeon feels that he or she is actually looking directly down onto the operating site. To that end, images of the tools 338, 339 may appear to be located substantially where the Surgeon's hands are located.

In addition, the real-time image is may be projected into a perspective image such that the Surgeon can manipulate the end effectors 322, 332 of the tools 338, 339 through their corresponding control devices 108, 109 as if viewing the workspace in substantially true presence. By true presence, it is meant that the presentation of an image is a true perspective image simulating the viewpoint of an operator that is physically manipulating the tools 338, 339. Thus, the processor 102 transforms the coordinates of the tools 338, 339 to a perceived position so that the perspective image is the image that one would see if the image capturing device 140 was located directly behind the tools 338, 339.

The processor 102 performs various functions in the system 100. One important function that it performs is to translate and transfer the mechanical motion of control devices 108, 109 to the teleoperational arm assembly 200 through control signals over bus 110 so that the Surgeon can effectively manipulate the tools 338, 339.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console the processor 102 may also comprise a number of subunits distributed throughout the system such as in printed circuit boards installed in the patient side cart 120 and/or the teleoperational arm assemblies 128, 129, 200, as well as, or alternatively to, the console 10.

For additional details on the construction and operation of various aspects of a medical teleoperational system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

Figure 2:
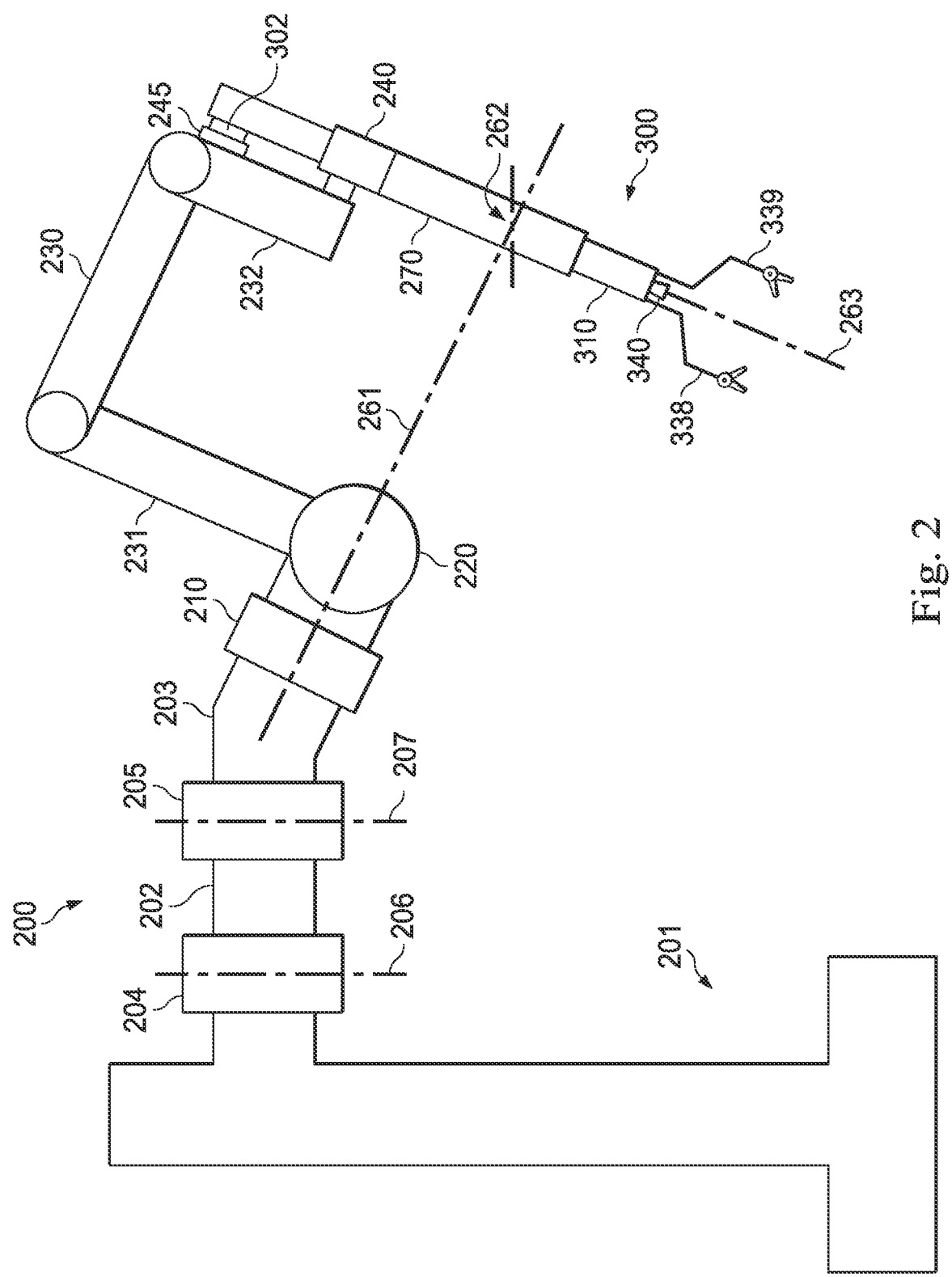
FIG. 2 is a simplified diagram of a teleoperational arm assembly holding a bundled unit of medical devices according to some embodiments.

FIG. 2 illustrates, as an example, a simplified side view (not necessarily in proportion or complete) of the teleoperational arm assembly 200 which is holding the bundled unit 300 of medical devices. A tool guide 270 is inserted through the minimally invasive incision 150 in the Patient and is coupled to the teleoperational arm assembly 200 by a guide holder 240. The bundled unit 300 may then be inserted into the Patient through the tool guide 270. The teleoperational arm assembly 200 is mechanically supported by a base 201 of the patient side cart 120.

Links 202, 203 are coupled together and to the base 201 through horizontal setup joints 204, 205. The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or fewer of each may be used as appropriate in this and other teleoperational arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The teleoperational arm assembly 200 also includes two active joints and a number of gears driven by motors. A yaw joint 210 allows arm section 230 to rotate around an axis 261, and a pitch joint 220 allows arm section 230 to rotate about an axis perpendicular to that of axis 261 and orthogonal to the plane of the drawing. An interface 302 comprises mating parts on the carriage 245 and the proximal end of the bundled unit 300 such as motor driven gears that actuate movement of the surgical tools 338, 339 and image capturing unit 340 through conventional joints, cable and pulley systems.

The arm section 230 is configured so that sections 231, 232 are always parallel to each other as the pitch joint 220 is rotated by its motor. As a consequence, the bundled unit 300 may be controllably moved by driving the yaw and pitch motors so as to pivot about the pivot point 262, which is generally located through manual positioning of the setup joints 204, 205 so as to be at the point of entry into the Patient. In addition, the bundled unit 300 is coupled to a carriage 245 on the arm section 230 which in turn is coupled to a linear drive mechanism to extend or retract the bundled unit 300 along its insertion axis 263.

Although each of the yaw joint 210, pitch joint 220 and motor driven gears in the carriage 245 is controlled by an individual joint or gear controller, the controllers may be controlled by a common master/slave control system so that the medical devices of the bundled unit 300 may be controlled through user (e.g., Surgeon or operator) manipulation of its associated control device.

FIG. 3 illustrates, as an example, a perspective view of a distal end of the bundled unit 300. The bundled unit 300 includes removable surgical tools 338, 339 for performing a medical procedure and a removable image capturing unit 340 for viewing the procedure at a surgical site within a patient. Each of the tools 338, 339 and image capturing unit 340 extends through a separate lumen formed in an inner core of the bundled unit 300. Replacement of one or both of the surgical tools 338, 339 during or in preparation for performing a medical procedure may then be accomplished by the Assistant removing the tool that is no longer needed from its lumen and replacing it with a substitute tool 131 from a tray 60 by inserting the substitute tool 131 in the vacated lumen. Alternatively, if unused lumens are available, an additional tool may be inserted through one of those available lumens without removing any other tools already in place.

The image capturing device 340 preferably includes a stereoscopic pair of cameras 342, 343 (and/or a single binocular camera) for three-dimensional imaging of the surgical site and an illuminating device 344 such as a light emitting diode (LED) or a fiber optics bundle carrying light from an external source, to enhance visibility of objects in the captured images. Auxiliary image capturing units, such as an ultrasound probe, may also be provided in available lumens of the bundled unit 300 for "seeing" into anatomic structures for surgical or diagnostic purposes.

In some embodiments, an overtube 310 is also included in the bundled unit 300 for protecting its inner core and the medical devices (i.e., surgical tools and image capturing units) inserted therethrough. The overtube 310 may be rigid. Alternatively, it may be formed of flexible material or comprise actively and/or passively bendable sections so that the bundled unit 300 may conform to the shapes of body lumens as it moves therethrough to a surgical site within a patient.

The surgical tools 338, 339 each have a controllably extendable, rotatable, and bendable arm to which their respective end effectors 322, 332 are coupled to by wrist mechanisms 323, 337. For example, the arm of the surgical tool 339 comprises three links 331, 333, 335 coupled by distal joints 334, 336. The proximal link 335 is controllably extendable and retractable along an insertion axis 352 (which is preferably parallel to the insertion axis 263 of the single-port device 300), and is controllably rotatable (as shown by rotation angle 353) about the insertion axis 352. The middle link 333, on the other hand, is controllably bendable by distal joint 336 relative to the link 335 (as shown by bend angle 351), and the distal link 331 is coupled to the links 333, 335 and bendable by distal joint 334 so that its bend angle 354 is in an opposite direction as that of the link 333 and consequently, keeps links 331, 335 in parallel alignment.

The arm of the surgical tool 338 is similarly constructed as that of the surgical tool 339. Additional details for one example of the wrist mechanisms 323, 337 are provided in commonly owned U.S. Pat. No. 6,817,974 "Surgical Tool Having Positively Positionable Tendon-Actuated Multi-Disk Wrist Joint," which is incorporated herein by this reference.

The image capturing device 340 also has a controllably extendable, rotatable, and bendable arm 345 that facilitates at least insertion/retraction of the image capturing unit 340 along its insertion axis (which may be parallel to the insertion axis 263 of the single-port device 300) and pitch motion in order to achieve a sufficient elevation of the image capturing device 340 "above" the surgical tools 338, 339 so as to properly view them during a surgical procedure. Additional degrees of freedom, such as roll angular movement of the image capturing device 340 about its insertion axis, may also be provided in order to facilitate additional positioning and orientation capabilities for the image capturing device 340. For enhanced maneuverability, the image capturing arm 345 may also be bendable such as the controllably bendable, rotatable, and extendable arms of the surgical tools 338, 339.

As medical procedures are conducted within the patient anatomy, the cameras 342, 343 of the image capturing device 340 may become fogged by, for example, by accumulated condensation. The fogged cameras may cause the image capturing device 340 to capture blurry or otherwise indistinct images. As described below, various systems and methods are provided minimize fogging of the cameras.

Figure 4:
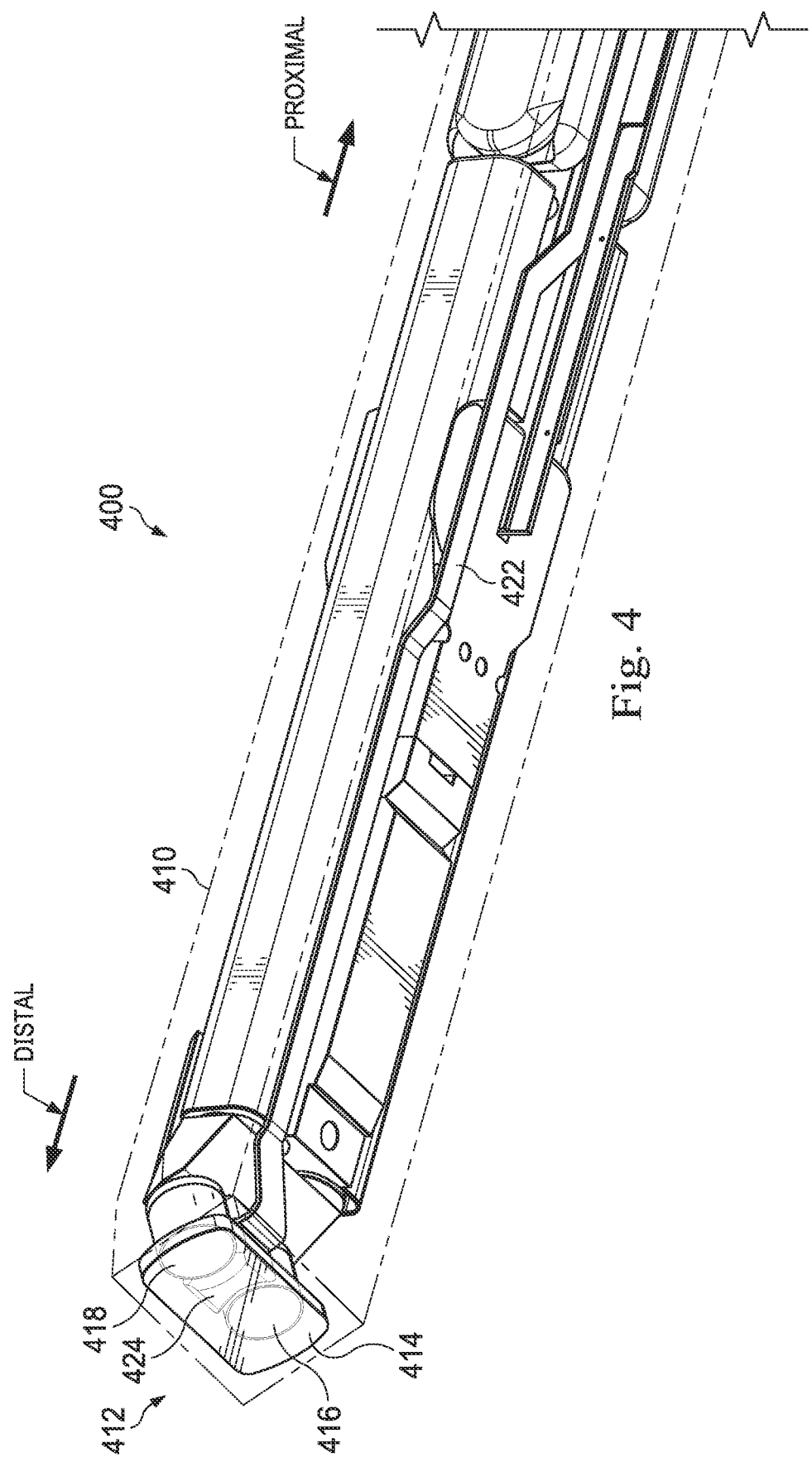
FIG. 4 illustrates an image capture device with a heat source for removing condensation from the window of the device, according to some embodiments.

FIG. 4 illustrates an image capturing device 400 that may minimize fogging. According to some embodiments consistent with FIGS. 1-3, image capturing device 400 may be used to implement image capturing device 340 of bundled unit 300. According to some embodiments, image capturing device 400 may be used in systems other than bundled unit 300.

Image capturing device 400 includes an elongated body 410 fully or partly enclosing components the image capturing device. In some examples, body 410 may correspond to an 8.8 mm endoscope shaft. More generally, the body 410 is sufficiently small to accommodate insertion/retraction of the image capturing device 400 through anatomical ports and/or anatomical passageways. According to some embodiments, body 410 may be formed using a rigid tube. In some embodiments, body 410 may be flexible. The cross-section of body 410 may be ellipsoidal, circular, polygonal, and/or any other suitable shape. In some examples, the width and/or the shape of body 410 may vary along the length. Although components of the image capturing device 400 are generally disposed within body 410, some components may protrude from the sides and/or out of the distal end 412.

A generally transparent window 414 is mounted at the distal end of the body 410. Optionally, the window 414 may be fitted within a metal housing (not shown) which is mounted at the distal end of the body 410. The window may be formed of a glass or polymer material. In this embodiment, the image capturing device 400 is an binocular image capturing device including optics component 416 spaced apart from an optics component 418. The optical components 416, 418 receive illumination (i.e., light and/or other electromagnetic signals) from a scene and project a pair of images onto an image sensor (not shown). The optical components 416, 418 may include one or more lenses, mirrors, apertures, filters, prisms, polarizers, and/or the like to achieve desired image characteristics (e.g., focal length and/or spectral characteristics).

Figure 5:
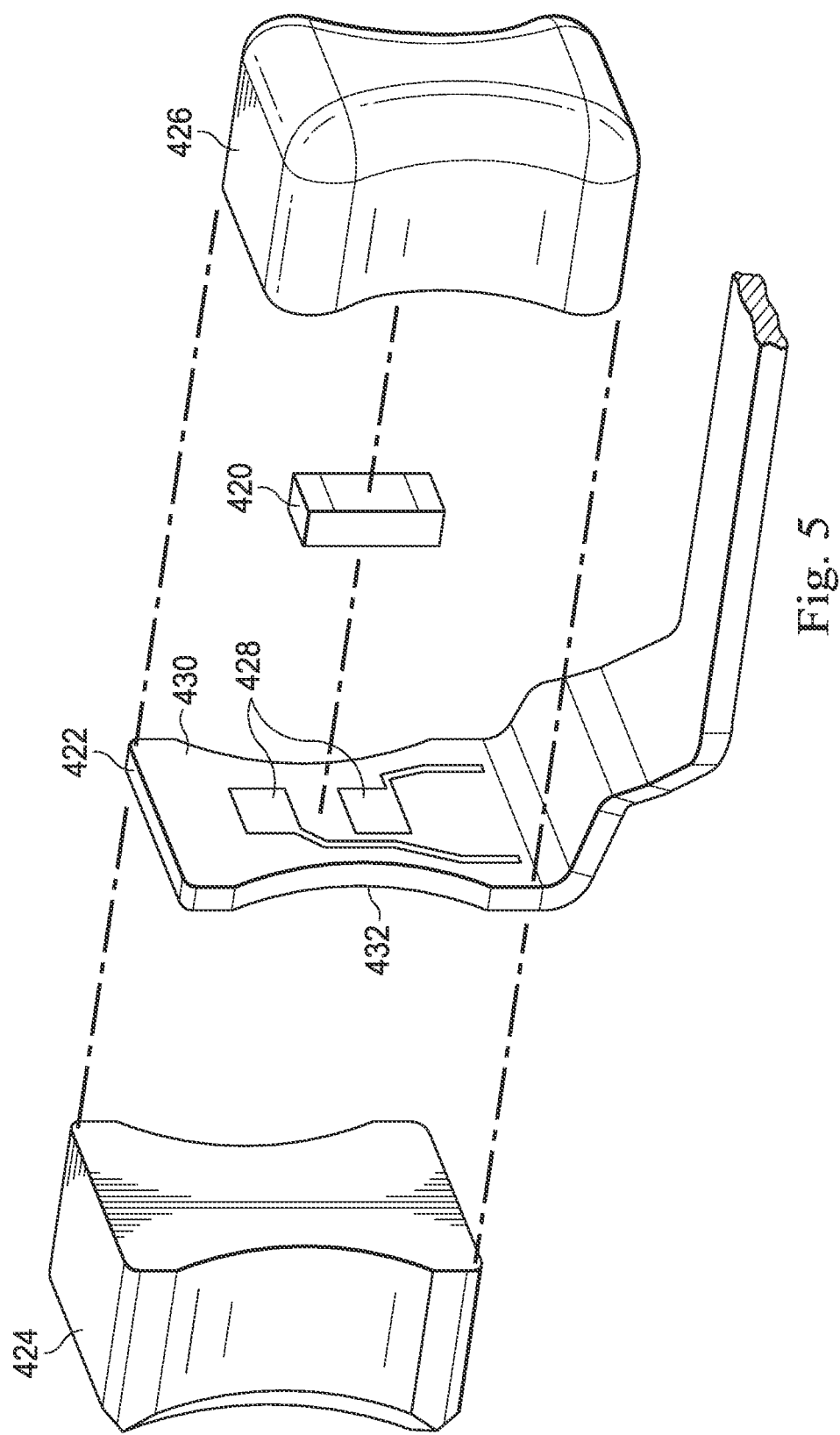
FIG. 5 illustrates an exploded image including a heat source and heat transfer system, according to some embodiments.

To prevent fogging of the window 414 or to remove or reduce the accumulation of condensation on the window, heat may be applied to the window. FIG. 5 illustrates an exploded image of including a heat source 420, a flexible circuit 422, a heat spreader 424, and a polymer spring 426. In this embodiment, the heat source 410 may be a resistor soldered to contacts 428 on a face 430 of the flexible circuit 422. The resistor may be a fixed value resistor. At a proximal end, the flexible circuit may be connected to a power supply within the body 410 or external of the body. The heat spreader 424 is soldered or otherwise coupled to the face 432 (opposite the face 430) of the flexible circuit 422. The heat spreader 424 extends between the optical components 416, 418 and contacts the window 414 or is placed in sufficiently close proximity that heat transfers from the spreader 424 to the window. The resistor 410 fits within a pocket in the spring 426. The spring 426 applies a force to the face 430 of the flexible circuit 422 to preload the heat spreader 424 against the window 414. This spring force allows the heat spreader 424 to maintain good thermal contact with the window 414. The heat spreader 424 may be coated or colored to reduce the light that is scattered from the heat spreader because scattered light may reduce the image quality. In various embodiments, the heat spreader 424 may be formed from copper. A thermal path is created as the heat from the resistor is transferred through the contacts 428 to the spreader 424 and then to the window 414.

In this embodiment, the resistor is a fixed value and the voltage from the power supply may be a fixed value. The resistor and voltage values may be selected to provide sufficient heat to minimize fogging of the window 414 while remaining at a temperature safe enough for use in contact with patient tissue for up to 30 minutes without burning or damaging the tissue. In various embodiments, the target temperature of the window 414 to reduce fogging may be between about 45° C. and 50° C.

The use of a fixed value resistor may minimize failure modes because no software or active control may fail. The only failure mode is a broken connection between the power source and the resistor which would result in a cooler, and thus safer, imaging device with a higher chance of fogging because of the lowered temperature. In other embodiments, active control of a variable resistor or other variable heat source may be suitable with sufficient safeguards.

Various thermal paths may carry the heat away from the window 414. For example, the heat may dissipate through the optical components 416, 418 and the other imaging components. This heat dissipation path passes through many different materials and joints which provide high resistance to heat transfer. As another example, the heat may dissipate through the outer body 410 and into the air or fluid around the body or along the length of the body. In this example heat may be dissipated within about 42 mm proximal of the window 414.

Figure 6:
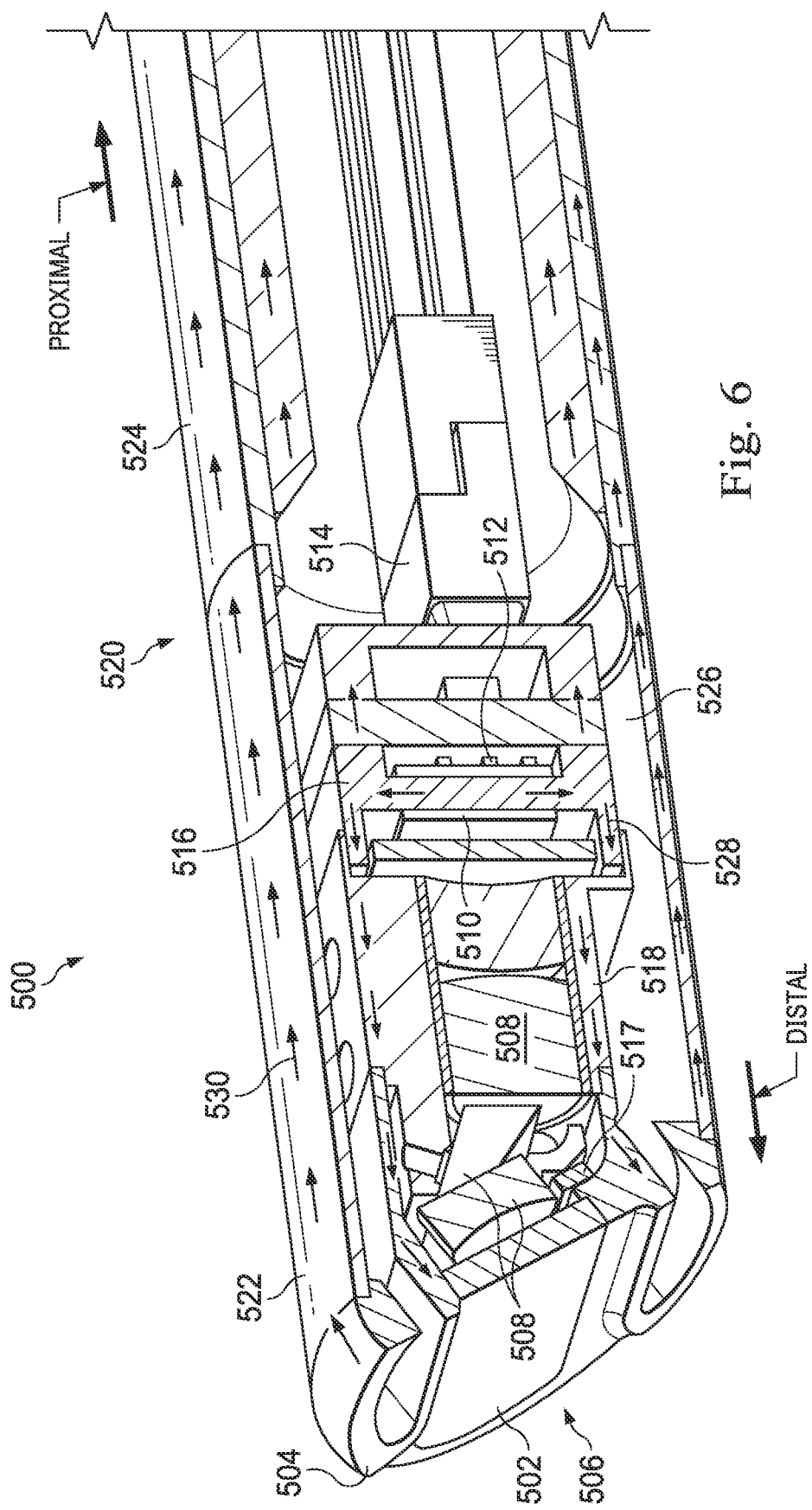
FIG. 6 illustrates an image capture device with a heat source for removing condensation from the window of the device, according to some embodiments.

FIG. 6 is a cross-sectional view of an image capturing device 500 that may minimize fogging. According to some embodiments consistent with FIGS. 1-3, image capturing device 500 may be used to implement image capturing device 340 of bundled unit 300. According to some embodiments, image capturing device 500 may be used in systems other than bundled unit 300.

This embodiment uses heat from heat-generating components of the imaging system to heat the window and reduce fogging. Image capturing device 500 includes window 502, fitted within a frame 504 at a distal end 506 of the device. The window may be formed of a glass or polymer material. In this embodiment, the image capturing device 500 includes optics components 508. The optical components 508 receive illumination (i.e., light and/or other electromagnetic signals) from a scene and project images onto an image sensor 510. The optical components 508 may include one or more lenses, mirrors, apertures, filters, prisms, polarizers, and/or the like to achieve desired image characteristics (e.g., focal length and/or spectral characteristics).

The image sensor 510 generally includes any device suitable for converting the projected images (including binocular images) from optical components 508 into analog and/or digital electrical signals that retain at least a portion of the information contained in the projected images. According to some examples, sensor 510 may include a charge coupled device (CCD) sensor, active pixel sensor, complementary metal oxide semiconductor (CMOS) sensor, N-type metal oxide semiconductor (NMOS) sensor and/or the like. According to some embodiments, sensor 508 may include a single monolithic sensor with dual active areas, and/or may include a plurality of discrete sensors.

The sensor 510 is electrically coupled to an image processor 512, which receives the electrical signals generated by the sensor and converts them for transmission. In some examples, image processor 512 may include signal conditioning electronics including one or more image signal processors (ISPs), amplifiers, analog to digital (A/D) converters, image encoders, and/or the like. In some examples, the output of image processor 512 may be a digital video signal feed. The digital video signal feed (or another signal representation of captured image data) is transmitted out of image capture device 500 via a connector 514. In some examples, connector 514 is configured to transmit image data and to receive power and/or control signals.

The sensor 510 and processor 512 are mounted to a housing 516, such as a ceramic circuit board. The optical components 508 are mounted to a housing 518, which may be a metal housing (e.g., a stainless steel housing). The housing 518 is connected between the housing 516 and the frame 504. The housing 518 serves as a hermetic seal for the optical components 508 and sensor 510 and provides a thermal path for heat energy generated by the sensor and processor 512.

Image capturing device 500 includes an elongated body 520 fully or partly enclosing components the image capturing device. The body 520 may be sufficiently small to accommodate insertion/retraction of the image capturing device 500 through anatomical ports and/or anatomical passageways. The body 520 includes a distal body portion 522 coupled to a proximal body portion 524. The body portion 522 may be formed of a metal such as stainless steel. The body portion 524 may be formed of a material that promotes more heat dissipation than the material of the distal body portion 522. For example, the body portion 524 may be formed of a stainless steel and copper composite. The frame 504 is connected to the distal end of the body portion 522. A gap 526 between the body portion 522 and the housing 518 may be filled with an insulating material such as air or another type of fluid or solid material.

A thermal path 528 is created as heat from the sensor 510 and the processor 512 are transferred through the housing 516, to the housing 518, to the frame 504, and to the window 502. The transferred heat removes fog from the window 502 and/or minimizes the accumulation of condensation. The heat is dissipated as it flows along a cooling thermal path 530 through the body portion 522 and to the heat sinking and heat spreading body portion 524. The body portion 524 allows heat to dissipate and reduces the risk of burning the patient.

Figure 7:
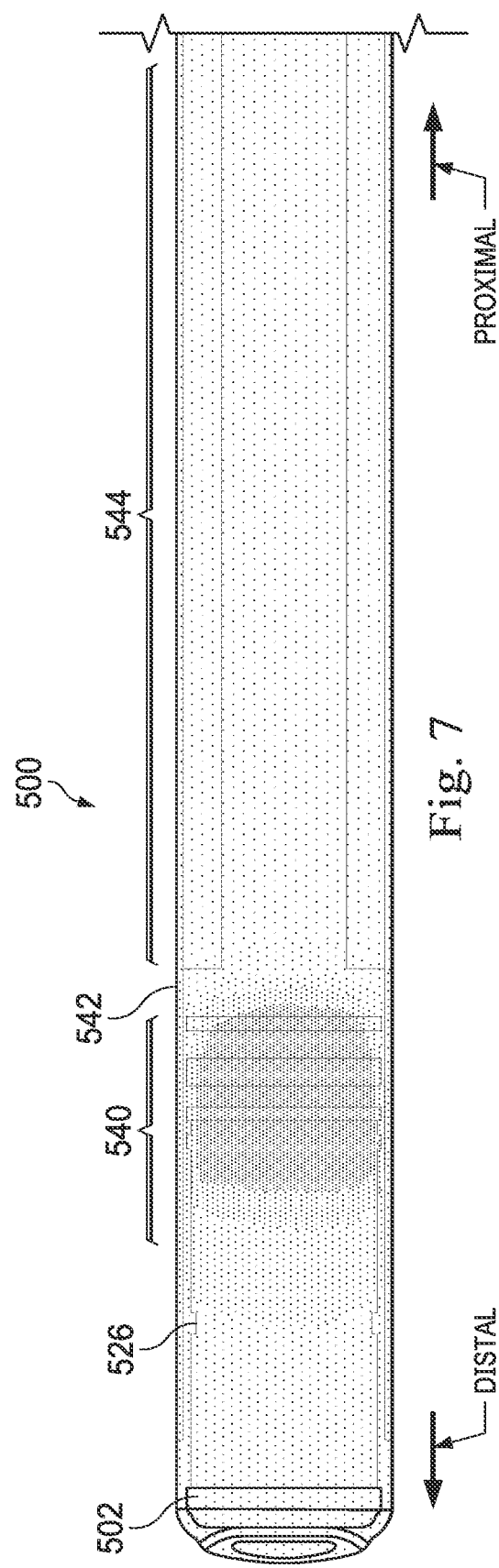
FIG. 7 illustrates a temperature gradient for the image capture device of FIG. 6.

In various embodiments, the target temperature of the window 414 to reduce fogging may be between about 45° C. and 50° C. FIG. 7 illustrates a temperature gradient for the image capturing device 500. The temperature is warmest in a region 540 corresponding to the location of the heat generating components 510, 512. As the heat is transferred to the distal body portion 522 and proximally toward the body region 524, it becomes dissipated. At a thermal safety zone 542 which corresponds generally with the distal end of the body portion 524, the temperature may be reduced to or below 42° C. The region 544 proximal of the safety zone 542 further dissipates the heat and may maintain a temperature at or below 42° C.

The image capturing device 500 may be considered to have a passive anti-fogging design in that it relies only on heat available from the heat generating components 510, 512. The surgical environment has a temperature of approximately 37° C. within the patient anatomy. This is a very controlled environment with predictable thermal dissipation properties. The design of device 500 is based on an energy balance of the input heat from the heat generating components and the surrounding environment to dissipate heat and maintain the window temperature at an equilibrium point. The device may be calibrated at the factory or otherwise prior to use. The heat supplied by the heat generating components may be adjusted by changing the input voltage/power to achieve the necessary energy balance.

In an alternative, actively-controlled embodiment, a temperature measuring device 517 may be used. The temperature measuring device may be mounted, for example, to the window, the housing or to another suitable location. Monitoring temperature with such a sensor would provide feedback to allow active power control of the heat generating components to regulate the temperature as conditions change. An actively controlled device may allow a quicker warm up to the equilibrium state. The thermal path may remain the same.

In various embodiments a temperature measuring device 517 may be, for example, a resistive thermal device (RTD), a thermistor, or a thermocouple-based device. An RTD may provide an accurate temperature data sensor and may have surface mount package sizes that are relatively small. Thermistors may also have a relatively small package surface mount design. Thermocouples may also be suitable but may be bulkier and report only relative temperature. Any of these example temperature measuring devices may be used by monitoring its resistance value and converting the measured resistance value to a corresponding temperature using a lookup table.

Certain challenges associated with the use of temperature measuring devices (such as RTDs and thermistors) may be mitigated. One challenge associated with temperature measuring devices may be self-heating. Driving a current through the temperature measuring device to measure resistance may cause the temperature measuring device itself to heat up, thereby causing a change in the measured resistance. Another challenge with temperature measuring devices may be that resistance in the wiring from the device to an analog monitoring circuit can create an error in the resistance reading. This error may be unique for each instrument, so for each instrument the temperature measuring device may be calibrated during the manufacturing process with an instrument-specific, resistance/temperature look-up table stored for each instrument.

The temperature measuring device may be located in any of a variety of locations in an image capturing device based upon packaging constraints and measurement accuracy needs. In one embodiment, the temperature measuring device may be placed against the window of the image capturing device to directly monitor window temperature. In an alternative embodiment, a temperature measuring device may be placed in contact with metal around the tip of the image capturing device (e.g., within approximately 5 mm of the distal end). The temperature of the metal around the tip may be less than about a degree from the temperature of the window itself. Generally, the further the temperature measuring device is from the window, the larger the offset between the window temperature and the sensor reading. Calibration may be determined during manufacturing or during simulations to determine the offset for each image capturing device. The greater the distance and the offset, the less reliable the sensor reading may be for use in a closed-loop control system. For example, distances of greater than 10 mm between the sensor and the window, in some image capturing devices, may prove unreliable in a closed-loop control system.

The temperature measuring device may be used within a closed-loop temperature control system in which the operation of the heat source is controlled based upon feedback from the temperature measuring device. A predetermined operation temperature or range of effective operating temperatures may be pre-established and monitored by the temperature measuring device to control the heat source to maintain the effective operating temperature. A closed-loop control system may reduce the variability of tip temperature, thus improving safety and effectiveness.

Temperature monitoring may be used within a temperature control system of an image capturing device to increase the device safety and effectiveness. For example, temperature monitoring may be used to control the tip heating power either as an on/off controller (e.g., if only a single voltage or current drives the heating element) or as an analog controller (e.g., if the voltage or current driving the heating element is adjustable). For example, temperature monitoring may be used to disable tip heating if a fault occurs in the image capturing device or if an unsafe situation is detected by the image capturing device (e.g., if tissue is directly contacted or if illumination is powered off, thus risking direct tissue contact). For example, temperature monitoring in a closed or open loop control system allows for adjustment of the distal tip heating to maintain the desired temperature and avoid overheating even if the surgical environment temperature significantly differs from the calibration environment temperature. For example, a common type of temperature monitoring sensor may be used with image capturing devices with different types of cooling systems. For example, a temperature sensor may be used to limit the magnitude of tip heating when the tip heat is adjustable based on fog detecting and or when the tip temperature in influenced by other heat sources such as a cautery instrument. For example, when illumination intensity is dynamic or adjustable, the amount of tip heating (and consequently window defogging) from illumination will also change. Temperature monitoring may be used to adjust the tip heating to maintain sufficient heat for defogging, even as the heat from illumination is variable. For example, the temperature monitoring may be built into a circuit, unconnected to the firmware or operating software of the image capturing system, to maintain a predetermined temperature. Optionally, the temperature may be monitored by firmware/software for logging purposes or emergency shutdown of the image capturing device even if the heating element itself is not adjustable.

Figure 8:
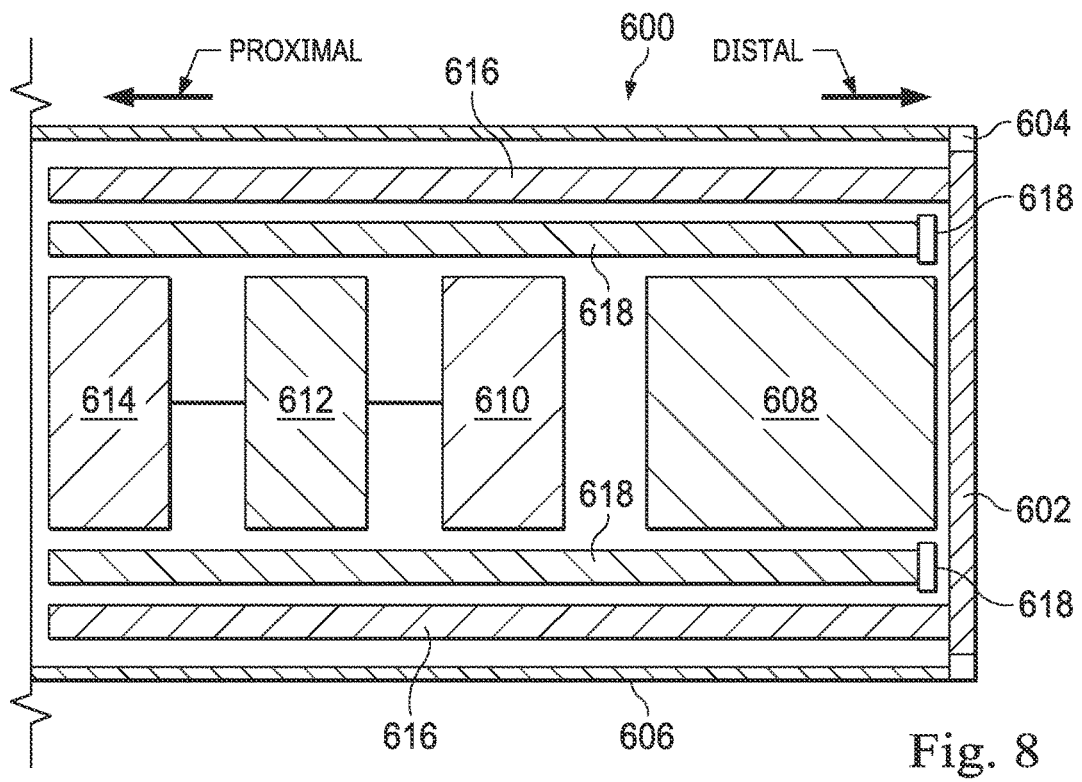
FIG. 8 illustrates a simplified cross-sectional diagram of an image capture device using visible light as a heat source, according to some embodiments.

FIG. 8 illustrates a simplified cross-sectional diagram of an image capturing device 600 using visible light as a heat source to minimize fogging. According to some embodiments consistent with FIGS. 1-3, image capturing device 600 may be used to implement image capturing device 340 of bundled unit 300. According to some embodiments, image capturing device 600 may be used in systems other than bundled unit 300. The image capturing device 600 includes a window 602 optionally coupled by a frame 604 to an elongated body 606. As described above, optical components 608 transmit illumination to an image sensor 610 which converts light to electrical signals for processing by a processor 612. The processor 612 is coupled to a power supply 614.

Illumination components 616 provide visible wavelengths of light to the anatomic area distal of the window 602. In some embodiments, illumination components 616 may include one or more illumination sources, such as optical fibers for transmitting visible light. Alternatively, the illumination components may include light emitting diodes (LEDs).

In this embodiment, a heat source is a plurality of dead-headed optical illumination fibers 618 which convey visible light to one or more components 620. The component 620 may be a metal or ceramic platform which absorbs the visible light transmitted by the fibers 618 and converts the light to heat. The heat from the component 620 warms the window 602 and removes fog and/or minimizes the accumulation of condensation.

In this embodiment the fibers 618 terminate proximally of the distal end of the illumination components 616. In one example, if 100 mW of heating is desired at the window 602, and 1000 optical fibers are used to deliver 1000 mW of light, then 100 of the fibers (e.g. fibers 618) would be dead headed such that 100 mW of light is converted to heat and 900 of the fibers (e.g., illumination component 616) would carry 900 mW of light for imaging illumination. All light from the fibers 618 is absorbed to prevent stray light from reducing image quality.

Figure 9:
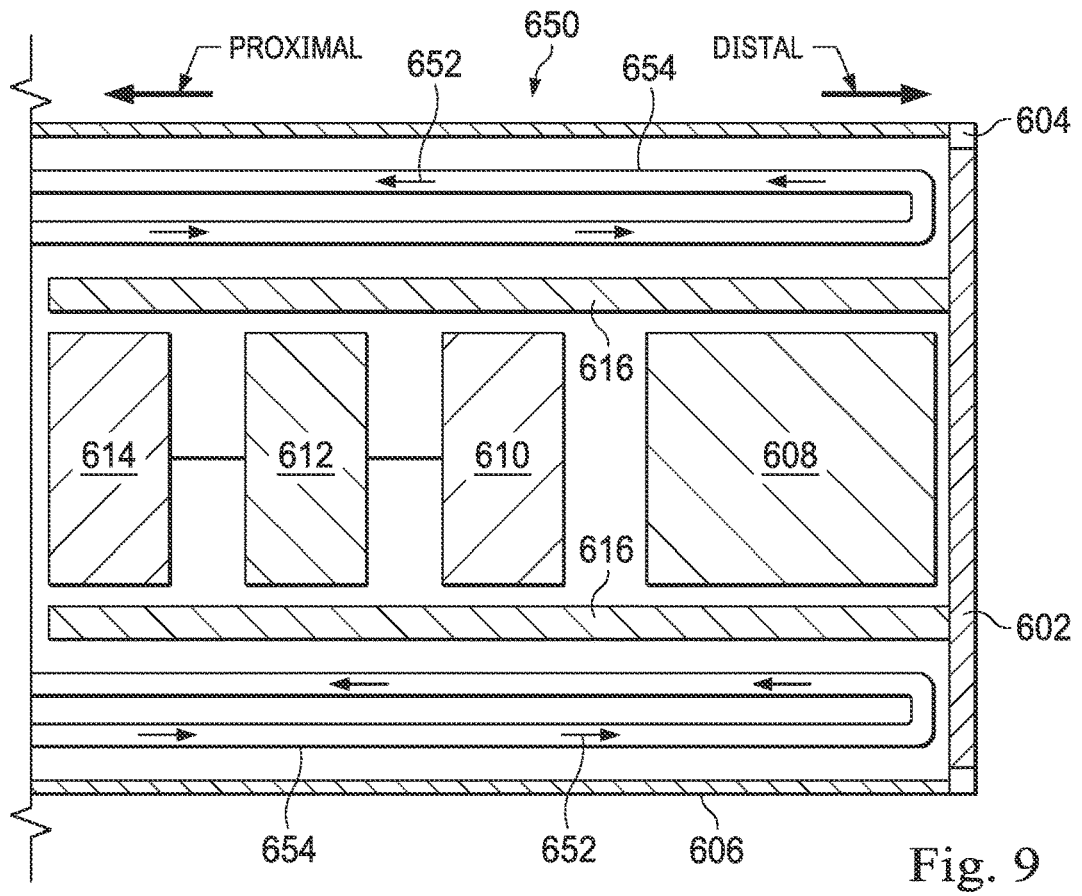
FIG. 9 illustrates a simplified cross-sectional diagram of an image capture device using a fluid as a heat source, according to some embodiments.

FIG. 9 illustrates a simplified cross-sectional diagram of an image capturing device 650 using a fluid as a heat source. The window 602, frame 604, elongate body 606, optical components 608, sensor 610, processor 612, power supply 614, and illumination components 616 are substantially the same as earlier described. In this embodiment, a heat source is a warm fluid 652 circulating through the body 606 of the device 650 to provide heat to the window 602 and/or the frame 604. The fluid 652 may be, for example, water, air, or saline. The fluid 652 may circulate through channels 654 that pass near the window 602 and frame 604. In this embodiment, the fluid 652 heats the internal, proximal surface of the window 602 or the frame 604 to remove fog and/or minimize the accumulation of condensation.

Figure 10:
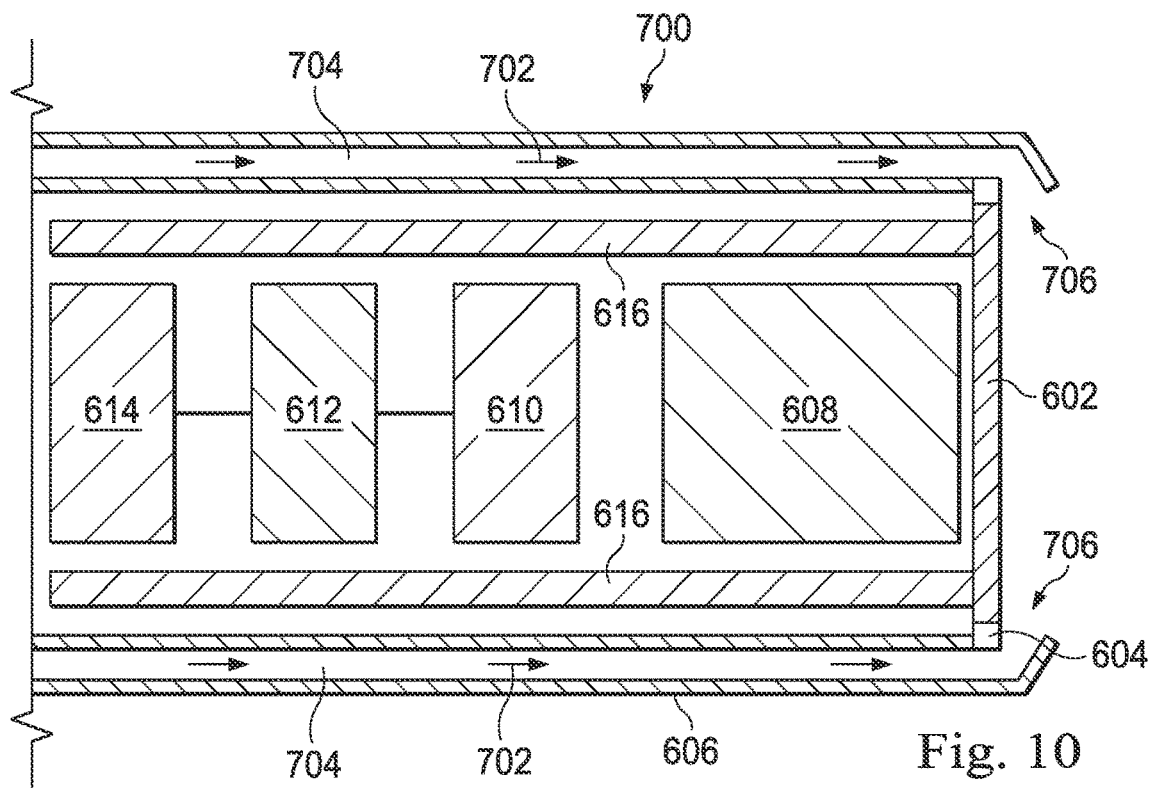
FIG. 10 illustrates a simplified cross-sectional diagram of an image capture device with a fluid applied to a distal window surface, according to some embodiments.

FIG. 10 illustrates a simplified cross-sectional diagram of an image capturing device 700 using a fluid as a heat and/or drying source. The window 602, frame 604, elongate body 606, optical components 608, sensor 610, processor 612, power supply 614, and illumination components 616 are substantially the same as earlier described. In this embodiment, a heat source is a warm fluid 702 that flows in a channel 704 and through an aperture 706 to an external surface of the window 602. The fluid 702 may be, for example, water, air, or saline. In this embodiment, the fluid 702 heats and/or dries the external, distal surface of the window 602 or the frame 604 to remove fog and/or minimize the accumulation of condensation.

Figure 11:
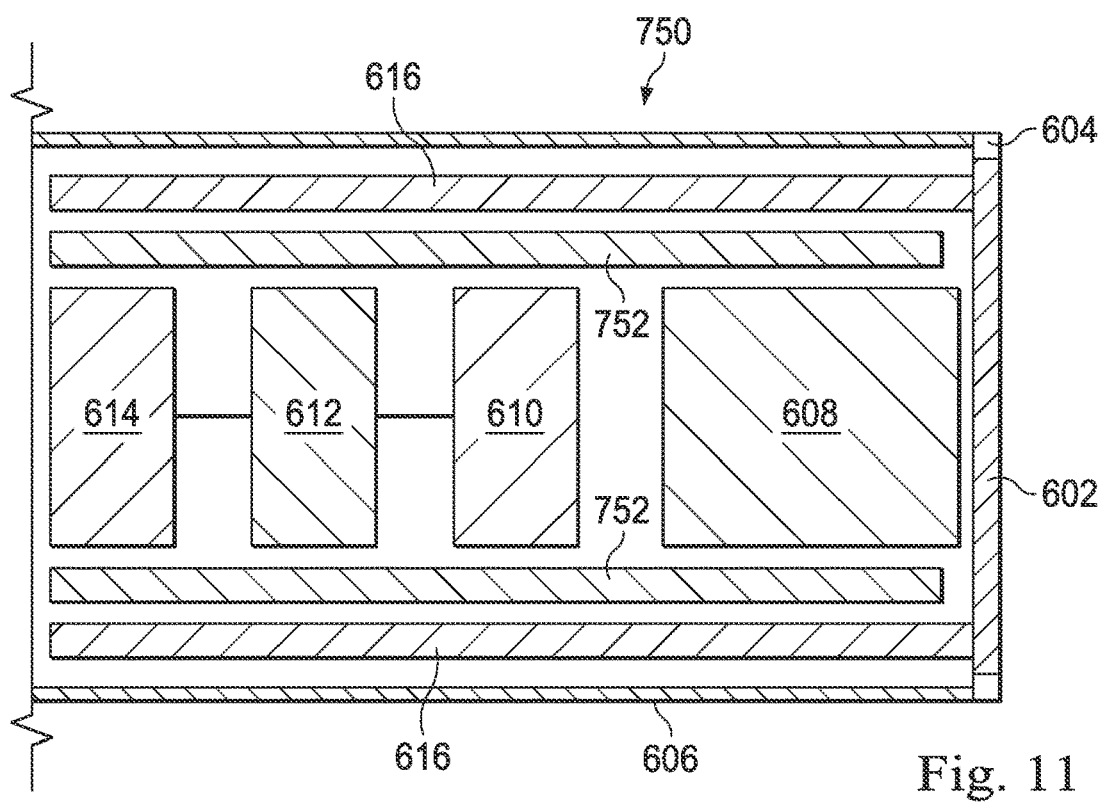
FIG. 11 illustrates a simplified cross-sectional diagram of an image capture device using infrared light as a heat source, according to some embodiments.

FIG. 11 illustrates a simplified cross-sectional diagram of an image capturing device 750 using an infrared light source 752 as a heating source. The window 602, frame 604, elongate body 606, optical components 608, sensor 610, processor 612, power supply 614, and illumination components 616 are substantially the same as earlier described. In this embodiment, the infrared light source 752 is an optical fiber transmitting light in the infrared wavelengths. The infrared light is aimed at the window 602 or the frame 604 to generate heat for removing fog and/or minimizing the accumulation of condensation. For example, an infrared wavelength longer than 8 µm may be fully absorbed by a sapphire window.

Figure 12:
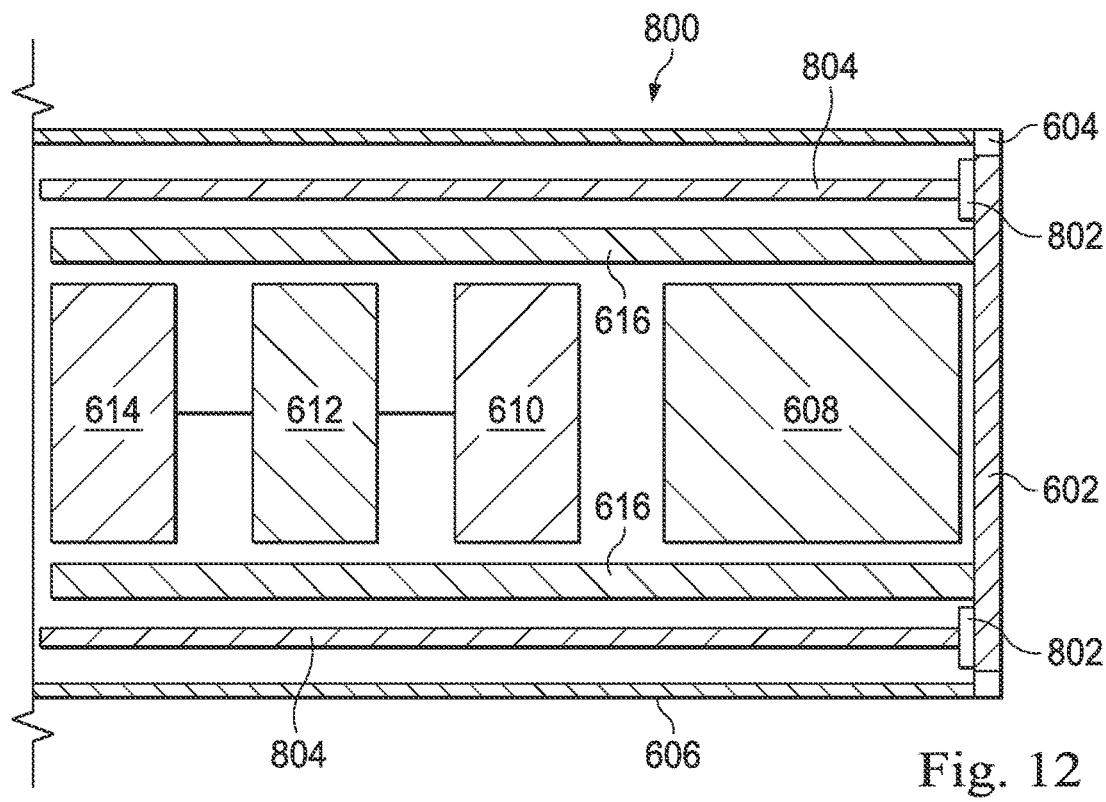
FIG. 12 illustrates a simplified cross-sectional diagram of an image capture device using a resistive heat source, according to some embodiments.

FIG. 12 illustrates a simplified cross-sectional diagram of an image capturing device 800 using electrical conductors 802 on the window 602 or frame 604 as a heating source. The window 602, frame 604, elongate body 606, optical components 608, sensor 610, processor 612, power supply 614, and illumination components 616 are substantially the same as earlier described. In this embodiment, electrical conductors 802 attached to the window 602 or frame 604 are powered by power supply components 804 (e.g., wires) to resistively heat the window for removing fog and/or minimizing the accumulation of condensation. As compared to the heat spreader 624, the electrical conductors 802 may require less power to defog the window 602. A lower power requirement improves the margin of safety for the patient. The electrical conductors may be transparent using indium tin oxide (ITO) or nanomaterials such as nano-silver or carbon nanotubes. Alternatively, the electrical conductors may be metal traces outside the field of view of the optical components.

Figure 13:
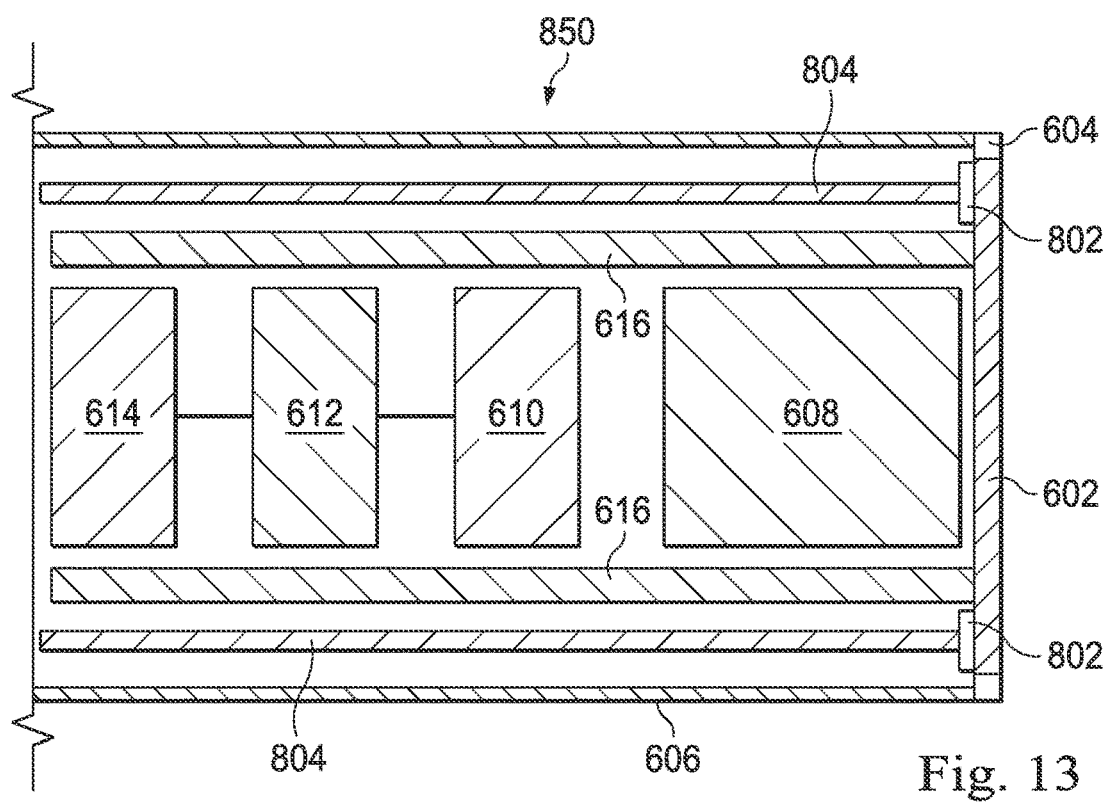
FIG. 13 illustrates a simplified cross-sectional diagram of an image capture device using ultrasonic energy to remove condensation from the window of the device, according to some embodiments.

FIG. 13 illustrates a simplified cross-sectional diagram of an image capturing device 850 using an ultrasonic transducer 852 to apply ultrasonic energy to the window 602. The window 602, frame 604, elongate body 606, optical components 608, sensor 610, processor 612, power supply 614, and illumination components 616 are substantially the same as earlier described. In this embodiment, ultrasound transducer 852 is powered by power supply components 854 (e.g., wires). The ultrasonic energy applied to the window 602 may vaporize the condensed fluid and clear the imaging field of view.

Figure 14:
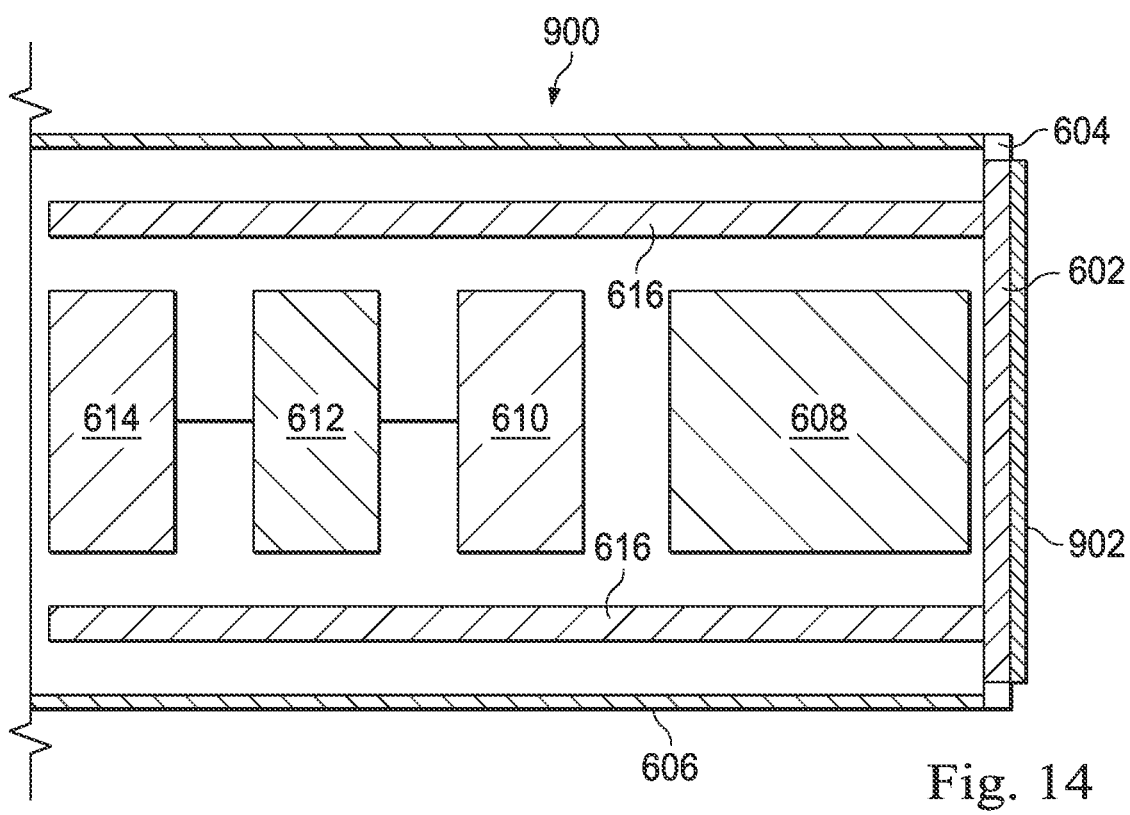
FIG. 14 illustrates a simplified cross-sectional diagram of an image capture device with a coated window, according to some embodiments.

FIG. 14 illustrates a simplified cross-sectional diagram of an image capturing device 900 with a coating 902 on an external surface of the window 602. The window 602, frame 604, elongate body 606, optical components 608, sensor 610, processor 612, power supply 614, and illumination components 616 are substantially the same as earlier described. In this embodiment, the coating 902 may be hydrophobic, causing the condensation to fall away from the window or may be hydrophilic, causing the condensation to create a thin film on the window. The coating 902 may be a deposition of nanoparticles, such as SiO2, that are smaller than the visible wavelength of light and will act to create a super-hydrophilic surface. Alternatively, the coating could be an etch process on a sapphire window to create peaked structures that are smaller than the visible wavelength of light and that act to create a super-hydrophilic surface. An etched surface may include the additional benefit of being integral to the window surface itself so coating adhesion and biocompatibility issues are reduced.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. An image capturing device, comprising:
    a first elongated body portion formed of a first material;
    a second elongated body portion coupled to a proximal end of the first elongated body portion, the second elongated body portion formed of a second material, wherein the second material has a greater heat conductivity than the first material;
    an imaging window coupled to a distal end of the first elongated body portion;
    a first housing within the first elongated body portion;
    an image sensor mounted to a distal facing surface of the first housing;
    an image processor mounted to the first housing and coupled to receive electrical signals from the image sensor; and
    a second housing within the first elongated body portion, the second housing coupled to the first housing and to the imaging window, wherein the second housing is configured to transmit heat generated by the image sensor and image processor to the imaging window.

2. The image capturing device of claim 1, wherein the first housing is formed of a ceramic material and the second housing is formed of a metal material.

3. The image capturing device of claim 1, wherein an insulating material extends between the first elongated body portion and the second housing.

4. The image capturing device of claim 3, wherein the insulating material is air.

5. The image capturing device of claim 1, wherein the first material is stainless steel and the second material is a copper and stainless steel composite.

6. The image capturing device of claim 1, further comprising a lens, wherein the lens is mounted to the second housing.

7. The image capturing device of claim 1, further comprising a temperature measurement device for sensing temperature at the distal end.

8. The image capturing device of claim 7, further comprising a heat source and a closed-loop temperature control system configured to control operation of the heat source based on the sensed temperature from the temperature measuring device.

9. The image capturing device of claim 1, wherein the image processor is mounted to a proximal facing surface of the first housing.

10. The image capturing device of claim 1, further comprising a frame coupled to the distal end of the first elongated body portion, wherein the imaging window is coupled to the frame.

11. The image capturing device of claim 1, wherein the second housing is a hermetic seal for the image sensor.

12. An image capturing device, comprising:
    an elongated body portion comprising:
        a distal elongated body portion; and
        a proximal elongated body portion coupled to the distal elongated body portion,
        wherein the proximal elongated body portion has a greater heat conductivity than the distal elongated body portion;
    an imaging window coupled to a distal end of the elongated body portion;
    a first housing within the elongated body portion;
    an image sensor mounted to a distal facing surface of the first housing;
    an image processor mounted to the first housing and coupled to receive electrical signals from the image sensor; and
    a second housing within the elongated body portion, the second housing coupled to the first housing and to the imaging window, wherein the first housing and the second housing are configured to transmit heat generated by the image sensor and the image processor to the imaging window.

13. The image capturing device of claim 12, wherein the first housing is formed of a ceramic material and the second housing is formed of a metal material.

14. The image capturing device of claim 12, further comprising a frame coupled to the distal end of the elongated body portion, wherein the imaging window is coupled to the frame.

15. The image capturing device of claim 12, wherein the distal elongated body portion is formed of stainless steel and the proximal elongated body portion is formed of a copper and stainless steel composite.

16. The image capturing device of claim 12, wherein the image processor is mounted to a proximal facing surface of the first housing.

* * * * *